(12) United States Patent
McKown et al.

(10) Patent No.: US 10,912,830 B2
(45) Date of Patent: Feb. 9, 2021

(54) METHODS AND REAGENTS FOR DIAGNOSING SJÖGREN'S SYNDROME

(71) Applicant: James Madison University, Harrisonburg, VA (US)

(72) Inventors: Robert L McKown, Bridgewater, VA (US); Kyle Seifert, Harrisonburg, VA (US); Ronald W Raab, Harrisonburg, VA (US)

(73) Assignee: JAMES MADISON INNOVATIONS, INC., Harrisonburg, VA (US)

( * ) Notice: Subject to any disclaimer, the term of this patent is extended or adjusted under 35 U.S.C. 154(b) by 370 days.

(21) Appl. No.: 15/886,716

(22) Filed: Feb. 1, 2018

(65) Prior Publication Data

US 2018/0214545 A1 Aug. 2, 2018

Related U.S. Application Data (60) Provisional application No. 62/453,383, filed on Feb. 1, 2017.

(51) Int. Cl.
| | |
|---|---|
| *G01N 33/68* | (2006.01) |
| *A61K 39/395* | (2006.01) |
| *G01N 33/53* | (2006.01) |
| *C07K 16/44* | (2006.01) |
| *C07K 14/47* | (2006.01) |
| *C07K 16/22* | (2006.01) |

(52) U.S. Cl.
CPC .......... *A61K 39/3955* (2013.01); *C07K 14/47* (2013.01); *C07K 14/473* (2013.01); *C07K 16/22* (2013.01); *C07K 16/44* (2013.01); *G01N 33/5308* (2013.01); *G01N 33/68* (2013.01); *C07K 2317/34* (2013.01)

(58) Field of Classification Search
None
See application file for complete search history.

(56) References Cited

FOREIGN PATENT DOCUMENTS

WO WO 2015/138604 * 9/2015

OTHER PUBLICATIONS

Aluru SV, Agarwal S, Srinivasan B, et al. Lacrimal praline rich 4 (LPRR4) protein in the tear fluid is a potential biomarker of dry eye Syndrome. PLoS One 2012;7:e51979.

Zhang Y, Wang N, Raab RW, McKown RL, Irwin JA, Kwon I, van Kuppevelt TH, Laurie GW. (2013). Targeting of heparanase-modified syndecan-1 by prosecretory mitogen laciitin requires conserved core GAGAL plus heparan and chondroitin sulfate as a novel hybrid binding site that enhances selectivity. J Biol Chem. 288:12090-101.

Cruzat A, Pavan-Langston D, Hamrah P. In vivo confocal microscopy of corneal nerves: analysis and clinical correlation. Semin Ophthalmol 2010;25:171-7.

Dartt DA. Neural regulation of lacrimal gland secretory processes: relevance in dry eye diseases. Prog Retin Eye Res 2009;28:155-77.

(Continued)

*Primary Examiner* — Rebecca M Giere
(74) *Attorney, Agent, or Firm* — Leveque IP Law, P.C.

(57) ABSTRACT

The inventive subject matter relates to novel antibodies to lacritin splice variants, improved methods for detecting lacritin splice variants, and methods for diagnosing Sjögren's Syndrome.

4 Claims, 5 Drawing Sheets

Specification includes a Sequence Listing.

(56) References Cited

OTHER PUBLICATIONS

Del Castillo JMB, Wasfy MA, Fernandez C, Garcia-Sanchez J. An in vivo confocal masked study on corneal epithelium and subbasal nerves in patients with dry eye. Invest Ophthalmol Vis Sci 2004;45:3030-3035.
Degasperi A, Birtwistle MR, Volinsky N, Rauch J, Kolch W, Kholodenko BN. Evaluating strategies to normalise biological replicates of Western blot data. PLoS One 2014;9:e87293.
Erie JC, McLaren JW, Hodge DO, Bourne WM. Recovery of corneal subbasal nerve density after PRK and LASIK. Am J Ophthalmol 2005;140:1059-1064.
Eskandari F, Webster JI, Sternberg EM. Neural immune pathways and their connection to inflammatory diseases. Arthritis Res Ther 2003;5:251-65.
Fujii A, Morimoto-Tochigi A, Walkup RD, Shearer TR, Azuma M. Lacritin-induced secretion of tear proteins from cultured monkey lacrimal acinar cells. Invest Ophthalmol Vis Sci 2013;54:2533-40.
Karnati R, Laurie DE, Laurie GW. Laciitin and the tear proteome as natural replacement therapy for dry eye. Exp Eye Res. Dec. 2013;I 17:39-52.
Knox SM, Lombaert IM, Haddox CL, et al. Parasympathetic stimulation improves epithelial organ regeneration. Nat Commun 2013;4:1494.
Koo BS, Lee DY, Ha HS, Kim JC, Kim CW. Comparative analysis of the tear protein expression in blepharitis patients using two-dimensional electrophoresis. J Proteome Res. May-Jun. 2005;4(3):719-24.
Labbe A, Liang Q, Wang Z, et al. Corneal nerve structure and function in patients with non-Sjogren dry eye: clinical correlations. Invest Ophthalmol Vis Sci 2013;54:5144-5150.
Laurie, G.W., Olsakovsky, L.A., Conway, B.P., McKown, R.L., Kitagawa, K., and Nichols, J.J. (2008) Dry Eye and Designer Ophthalmic Treatments. Optom Vis Sci. 85(8):643-52.
Ma, P., S.L. Beck, R.W. Raab, R.L. McKown, G.L. Coffman, A. Utani, W.J.Chirico, A.C. Rapraeger, and G.W. Laurie. (2006) Heparanase deglycanation of syndecan-1 is required for binding of epithelial-restricted prosecretory mitogen "lacritin". J. Cell Biol. 174(7): 1097-1106.
McKown RL, Coleman Frazier EV, Zadrozny KK, et al. A cleavage-potentiated fragment of tear lacritin is bactericidal. J Biol Chem 2014;289:22172-82.
McKown RL, Wang N, Raab RW, et al. Lacritin and other new proteins of the lacrimal functional unit. Exp Eye Res 2009;88:848-58.
McNamara NA, Ge S, Lee SM, Enghauser AM, Kuehl L, Chen FY, Gallup M, McKown RL. Reduced Levels of Tear Lacritin Are Associated With Corneal Neuropathy in Patients With the Ocular Component of Sjogren's Syndrome. Invest Ophthalmol Vis Sci. Oct. 1, 2016;57(13):5237-5243.
Nichols JJ, Green-Church KB. Mass spectrometry-based proteomic analyses in contact lens related dry eye. Cornea 2009;28:1109-17.
Oliveira-Soto L, Efron N. Morphology of corneal nerves in soft contact lens wear. A comparative study using confocal microscopy. Ophthalmic Physiol Opt 2003;23:163-74.
Olofsson PS, Rosas-Ballina M, Levine YA, Tracey KJ. Rethinking inflammation: neural circuits in the regulation of immunity. Immunol Rev 2012;248:188-204.
Patel DV, Tavakoli M, Craig JP, Efron N, McGhee CN. Corneal sensitivity and slit scanning in vivo confocal microscopy of the subbasal nerve plexus of the normal central and peripheral human cornea. Cornea 2009;28:735-740.
Patel SV, McLaren JW, Hodge DO, Bourne WM. Confocal microscopy in vivo in corneas of long-term contact lens wearers. Invest Ophthalmol Vis Sci 2002;43:995-1003.
Rhiner C, Gysi S, Frohli E, Hengartner MO, Hajnal A. Syndecan regulates cell migration and axon guidance in C. elegans. Development 2005;132:4621-33.
Zhang M, Chen J, Luo L, Xiao Q, Sun M, Liu Z. Altered corneal nerves in aqueous tear deficiency viewed by in vivo confocal microscopy. Cornea 2005;24:818-24.
Samudre S, Lattanzio FA, Jr., Lassen V, et al. L 361 Lacritin, a novel human tear glycoprotein, promotes sustained basal tearing and is well tolerated. Invest Ophthalmol Vis Sci 2011;52:6265-70.
Sanghi S, Kumar R, Lumsden A, et al. cDNA and genomic cloning of lacritin, a novel secretion enhancing factor from the human lacrimal gland. J Mol Biol 2001;310:127-39.
Shiboski S, Shiboski C, Criswell L, et al. American College of Rheumatology classification criteria for Sjogren's Syndrome: A data-driven, expert consensus approach in the Sjogren's International Collaborative Clinical Alliance Cohort. Arthritis Care Res 2012;64:475-487.
Tavakoli M, Quattrini C, Abbott C, et al. Corneal confocal microscopy a novel noninvasive test to diagnose and stratify the severity of human diabetic neuropathy. Diabetes Care 2010;33:1792-1797.
Tuisku IS, Konttinen YT, Konttinen LM, Tervo TM. Alterations in corneal sensitivity and nerve morphology in patients with primary Sjtigren's Syndrome. Exp Eye Res 2008;86:879-885.
Tuominen IS, Konttinen YT, Vesaluoma MH, Moilanen JA, Helinto M, Tervo TM. Corneal innervation and morphology in primary Sjogren's Syndrome. Invest Ophthalmol Vis Sci 2003;44:2545-9.
Velez VF, Romano JA, McKown RL, et al. Tissue transglutaminase is a negative regulator of monomeric lacritin bioactivity. Invest Ophthalmol Vis Sci 2013;54:2123-32.
Vijmasi T, Chen FY, Balasubbu S, ct al. Topical administration of lacritin is a novel therapy for aqueous-deficient dry eye disease. Invest Ophthalmol Vis Sci 2014;55:5401-9.
Whitcher JP, Shiboski CH, Shiboski SC, et al. A simplified quantitative method for assessing keratoconjunctivitis sicca from the Sjtigren's Syndrome International Registry. Am J Ophthalmol 2010;149:405-415.
Villani E, Galimberti D, Viola F, Mapclli C, Ratiglia R. The cornea in Sjogrcn's Syndrome: an in vivo confocal study. Invest Ophthalmol Vis Sci 2007;48:2017-22.
Wang N, Zimmerman K, Raab RW, et al. Lacritin rescues stressed epithelia via rapid forkhead box 03 (FOXO3)-associated autophagy that restores metabolism. J Biol Chem 2013;288:18146-61.
Wang W, Jashnani A, Aluri SR, Gustafson .TA, Hsueh PY, Yarber F, McKown RL, Laurie GW, Hamm-Alvarez SF, MacKay .TA. A thermo-responsive protein treatment for dry eyes. J Control Release. Feb. 10, 2015;199:156-67.
Wang, J., Wang, N., Xie, J., Walton, S., McKown. R., Raab, R., Ma, P., Beck, S., Coffman, G., Hussaini, and Laurie, G. (2006) Restricted epithelial proliferation by lacritin via PKC-dependent NFAT and mTOR pathways. J. Cell Biol. 174(5): 889-700.

* cited by examiner

METHODS AND REAGENTS FOR DIAGNOSING SJÖGREN'S SYNDROME

CROSS-REFERENCE TO RELATED APPLICATIONS

This application claims the benefit of U.S. Provisional Patent Application No. 62/453,383, filed Feb. 1, 2017, the contents of which are hereby incorporated by reference in their entirety.

STATEMENT REGARDING FEDERALLY SPONSORED RESEARCH OR DEVELOPMENT

This work was supported by National Eye Institute grant RO1 EY024327. The United States government has rights in the inventive subject matter by virtue of this support.

REFERENCE TO A SEQUENCE LISTING

This application is filed with a Sequence Listing, which is filed electronically as an ASCII text file via EFS-Web and will thus serve as both the "paper" and "computer readable form" copies of the Sequence Listing. The name of the ASCII text file is "1074-6U_Sequence_Listing.txt", the date of creation is Feb. 1, 2018, and the size of the ASCII text file is 2,437 bytes. Applicants hereby incorporate by reference all materials in the ASCII text file "1074-6U_Sequence_Listing.txt" in their entirety.

Background of the Inventive Subject Matter

1. Field of the Inventive Subject Matter

The inventive subject matter relates to novel antibodies to lacritin splice variants, improved methods for detecting lacritin splice variants, and methods for diagnosing Sjögren's Syndrome.

2. Background

A healthy ocular surface is maintained in large part by a complex mixture of biologically active proteins found in tear film. Disruption of the delicate balance of tear proteins has been associated with a number of ocular diseases including Sjögren's Syndrome.

Sjögren's Syndrome is a long-term autoimmune disease in which many of the moisture-producing structures of the body are affected. This results primarily in the development of a dry mouth, difficulty eating dry foods, and/or dry eyes. Other symptoms can include dry skin, a chronic cough, vaginal dryness, numbness in the arms and legs, feeling tired, muscle and joint pains, and thyroid problems. Those affected also appear to be at increased risk of lymphoma. Patients with this condition may notice irritation, a gritty feeling, or painful burning in the eyes. Swelling of the glands around the face and neck are also common. Some patients experience dryness in the nasal passages, throat, vagina and skin. Swallowing difficulty and symptoms of acid reflux are also common.

So-called "primary" Sjögren's Syndrome occurs in people with no other rheumatic disease, while "secondary" Sjögren's occurs in people who have another rheumatologic disease, most often systemic lupus erythematosus or rheumatoid arthritis.

Most of the complications of Sjögren's Syndrome occur because of decreased tears and saliva. Patients with dry eyes are at increased risk for infections around the eye and may have damage to the cornea. Dry mouth may cause an increase in dental decay, gingivitis, and oral yeast infections that may cause pain and burning. Some patients have episodes of painful swelling in the saliva glands around the face. Additional complications in other parts of the body can occur, including pain and stiffness in the joints with mild swelling; vasculitis; inflammation in the lungs, liver, and kidney; non-specific numbness, tingling, and weakness; and inflammation of the parotid gland.

The precise etiology of Sjögren's Syndrome is not known, but it is an autoimmune disorder. While the exact cause is unclear, it is believed to involve a combination of genetics and environmental trigger(s). People with this disease have abnormal proteins in their blood. This suggests that the immune system, which normally functions to protect the body against cancers and infections, is reacting against its own tissue. The decrease in tears and saliva seen in Sjögren's Syndrome occurs when the glands that produce these fluids are damaged by inflammation. Research suggests that genetic factors and possibly viral infections may predispose people to developing this condition There is no simple method for diagnosing the presence or absence of Sjögren's Syndrome, and current methods can be complicated and invasive. Current clinical methods of diagnosis depend on a combination of symptoms, physical examination, blood tests, and special studies. Dry eyes and mouth may be early signs of the condition but require further investigation, because these symptoms can be caused by many other conditions or medications. Special tests may assess any decrease in tear or saliva production. An eye examination is helpful in detecting any eye physiological changes seen in Sjögren's. The most definitive diagnosis currently requires biopsy of moisture-producing glands and blood tests for specific antibodies typical of the disease, including anti-nuclear antibodies (ANA), anti-SSA and SSB antibodies, and/or rheumatoid factor, but these are not always present. Invasive biopsies of saliva glands around the face or under the surface of the inner lip also may be required to make a diagnosis.

At this time, Sjögren's Syndrome cannot be cured.

Thus, there is a critical need for simple, rapid, less-invasive, more cost-effective and more accurate methods for diagnosing ocular diseases such as Sjögren's Syndrome.

BRIEF SUMMARY OF THE INVENTION

Applicants have determined that identification and quantitation of key tear proteins can provide biomarkers for the diagnosis of Sjögren's Syndrome. Further, it is expected that reduced levels of critical tear proteins can be augmented by topical application of exogenous tear proteins and/or synthetic peptides in order to effectively treat Sjögren's Syndrome.

It has recently been reported that endogenous levels of the tear protein lacritin are dramatically reduced in patients suffering from Sjögren's Syndrome. Applicants have determined that quantitation of various lacritin species levels in tears are biomarkers for the clinical diagnosis of Sjögren's Syndrome.

Thus, the inventive subject matter relates to a method for detecting lacritin-c in a subject, comprising detecting whether lacritin-c is present in a tear sample from a human subject by contacting the tear sample with an anti-lacritin-c antibody and detecting binding between lacritin-c and the antibody.

The inventive subject matter also relates to a method for detecting lacritin in a subject, comprising detecting whether lacritin is present in a tear sample from a human subject by contacting the tear sample with an anti-lacritin antibody and detecting binding between lacritin and the antibody.

The inventive subject matter further relates to a method for diagnosing Sjögren's Syndrome in a subject, comprising: (a) detecting whether lacritin-c is present in a tear sample obtained from a human subject by contacting the tear sample with a non-human animal anti-lacritin-c antibody and detecting binding between lacritin-c and said antibody; and (b) diagnosing the subject with Sjögren's Syndrome when lacritin-c in the tear sample is not detected.

The inventive subject matter relates to an additional method for diagnosing Sjögren's Syndrome in a subject, comprising: (a) obtaining a tear sample from a human subject; (b) detecting whether lacritin is present in the tear sample by contacting the tear sample with antibody to SEQ ID NO. 1, and detecting binding between lacritin and said antibody to SEQ ID NO. 1; (c) detecting whether lacritin-c is present in the tear sample by contacting the tear sample with antibody to SEQ ID NO. 2 and detecting binding between lacritin-c and said antibody to SEQ ID NO. 2; and (d) diagnosing the subject with Sjögren's Syndrome when lacritin or lacritin-c in the tear sample is not detected.

Additionally, the inventive subject matter relates to a method for diagnosing Sjögren's Syndrome in a subject, comprising: (a) in a tear sample of a subject suspected to suffer from Sjögren's Syndrome, determining the amount of lacritin-c present in said tear sample with an immunoassay, wherein said immunoassay comprises: (i) contacting the sample with an anti-lacritin-c antibody; (ii) measuring the amount of bound lacritin-c in the sample; and (b) comparing the amount of lacritin-c with reference amount(s) obtained from one or more sample(s) of subject(s) known not to suffer from Sjögren's Syndrome, wherein Sjögren's Syndrome is diagnosed if the amount of lacritin-c is decreased as compared to said reference amount(s).

The inventive subject matter also relates to a method for diagnosing Sjögren's Syndrome in a subject, comprising: (a) in a tear sample of a subject suspected to suffer from Sjögren's Syndrome, determining the amount of lacritin and the amount of lacritin-c present in said tear sample with an immunoassay, wherein said immunoassay comprises: (i) contacting the sample with antibody microarray comprising an anti-lacritin antibody and an anti-lacritin-c antibody; (ii) measuring the amounts of bound lacritin and lacritin-c in the sample; and (b) comparing the amounts of lacritin and lacritin-c with reference amounts obtained from samples from subject(s) known not to suffer from Sjögren's Syndrome, wherein Sjögren's Syndrome is diagnosed if the amounts of either or both of lacritin and lacritin-c are decreased as compared to said reference amounts.

Finally, the inventive subject relates to a method for diagnosing Sjögren's Syndrome in a subject, comprising: (a) in a tear sample of a subject suspected to suffer from Sjögren's Syndrome, determining the amount of cross-linked lacritin polymers present in said tear sample with an immunoassay, wherein said immunoassay comprises: (i) contacting the sample with an anti-lacritin antibody; (ii) measuring the amount of bound lacritin polymers in the sample; and (b) comparing the amount of lacritin polymers with reference amount(s) obtained from one or more sample(s) of subject(s) known not to suffer from Sjögren's Syndrome, wherein Sjögren's Syndrome is diagnosed if the quantity of lacritin polymers is increased as compared to said reference amount(s).

DETAILED DESCRIPTION OF THE INVENTION

A. Definitions

The term "SEQ ID NO. 1" as used herein refers to the sequence

EDASSDSTGADPAQEAGTS.

The term "N-Term Antibody" as used herein refers to polyclonal antibodies produced in rabbit against SEQ ID NO. 1, the first 19 amino acids in the N-terminus of mature lacritin.

The term "Lacripep Antibody" as used herein refers to polyclonal antibodies produced in goat against 19 amino acids in the N-94/C-6 C-terminus of lacritin.

The term "SEQ ID NO. 2" as used herein refers to the sequence

SKSLSLCQINNLEKSLAAGPHHTSTHRDKPG.

The term "I3 Antibody" as used herein refers to polyclonal antibodies produced in rabbit against SEQ ID NO. 2, 31 amino acids in Intron 3 of lacritin-c.

The term "lacritin" as used herein refers to the naturally-occurring human monomeric protein having the following full 138 amino acid sequence, SEQ ID NO. 3:

```
1   MKFTTLLFLA AVAGALVYAE DASSDSTGAD PAQEAGTSKP NEEISGPAEP ASPPETTTTA

61  QETSAAAVQG TAKVTSSRQE LNPLKSIVEK SILLTEQALA KAGKGMHGGV PGGKQFIENG

121 SEFAQKLLKK FSLLKPWA
```

Upon secretion by acinar cells in the lacrimal gland, the first 19 amino acids are cleaved from the lacritin polypeptide as transcribed to produce "mature lacritin".

The term "immunoassay" as used herein refers broadly to ELISA-based methods, whether micro-plate ELISA-based, fully-automated or robotic immunoassay, latex agglutination assay, sandwich ELISA using a capture antibody and a detection antibody, or other similar ELISA-based methods known in the art. Preferably, the immunoassay system of the present inventive subject matter is based upon the infrared excitation/detection of fluorescent secondary antibodies with increased sensitivity, improved reproducibility, and quantification of banding patterns. Such a system offers the advantage of multiplex detection enabling analysis of more than one protein on the same blot, in particular providing a single test for lacritin and lacritin-c. The LI-COR Odyssey CLx Imaging System is one example of such a system.

The term "antibody" as used herein refers to a protein consisting of one or more polypeptides substantially encoded by immunoglobulin genes or fragments of immunoglobulin genes, and encompasses polyclonal antibodies, monoclonal antibodies, and fragments thereof, as well as molecules engineered from immunoglobulin gene sequences.

The term "tear sample" refers to the biological material being tested for and/or suspected of containing analyte(s) of interest. A tear sample may be used directly as obtained from the biological source or following a pretreatment to modify the character of the sample. If pretreatment is employed with respect to the tear sample, such pretreatment methods are such that the analyte of interest remains in the sample at a concentration proportional to that in an untreated sample. According to one aspect of the present inventive subject matter, the biological fluid is preferably obtained directly from the eye of a subject. A tear sample is obtained using any technique known in the art, preferably using Schirmer Tear Test strips such as those available from the Sjögren's International Collaborative Clinical Alliance.

A heathy ocular surface is maintained in large part by a complex mixture of biologically active proteins found in tear film. For example, tears collected on Schirmer Tear Test (SST) strips during routine clinical examinations provides an opportunity for biochemical analysis of the tear proteome to determine relative concentrations of human proteins secreted and collected in a cell-free environment. Applicants expect that tear proteins, such as lacritin and lacritin-c, accurately prognosticate ocular diseases and function as tear biomarkers for the diagnosis of Sjögren's Syndrome.

B. Inventive Methods for Detecting Lacritin-c

Lacritin is a 12.3 kDa endogenous tear prosecretory mitogen reported to be decreased in patients with various forms of dry eye disease. Lacritin is detected in tears as an active monomer of ~25 kDa, an active proteolytically cleaved fragment of ~12 to 15 kDa, and inactive, tissue transglutaminase-generated dimers, trimers, and larger polymers >40 kDa. The proteolytically cleaved fragment of lacritin releases a potent gram negative and positive bactericidal activity that functions under physiological conditions. Lacritin promotes basal tearing when topically applied to eyes of normal rabbits and rescues cultured human corneal epithelial cells from inflammatory cytokine stress, including stress induced by tears from dry eye patients. Topical administration of lacritin may be a novel therapy for aqueous-deficient dry eye disease.

Additionally, lacritin has two splice variants, lacritin-b and lacritin-c. Lacritin-b is a deletion of DNA coding for 13 amino acids in exon 4, which is then normally spliced in frame to exon 5. Lacritin-c is composed of coding sequences for the first three lacritin exons, into which is spliced an open reading frame coding for 39 amino acids derived from intron 3 (13), followed by a stop codon. The lacritin splice variants are translated into proteins and are present in human tears. The unique 39 amino acid sequence found in lacritin-c is not found in lacritin, which has provided Applicants an opportunity to create unique antibodies that will detect only lacritin-c in tear samples, for example using Western blot analysis as in the Examples herein.

Applicants used synthetic peptides to produce lacritin and lacritin-c specific polyclonal antibodies in rabbits, have determined that their anti-lacritin-c antibodies detect putative lacritin-c proteins in human tears, have determined that their anti-lacritin antibodies detect lacritin proteins in human tears, and have determined that the protein banding patterns in tears from Sjögren's Syndrome patients are different compared to normal tears.

The inventive subject matter thus relates to a method for detecting lacritin, lacritin-c, or both in a subject, comprising detecting whether lacritin or lacritin-c is present in a tear sample from a human subject by contacting the tear sample with an anti-lacritin antibody or an anti-lacritin-c antibody and detecting binding between lacritin or lacritin-c and the respective antibody. Lacritin and lacritin-c can be detected in the same assay, as lacritin-c lacks the C-terminus of full length lacritin associated with the biological activities of that tear protein, and has a different N-terminus from full length lacritin.

C. Inventive Methods for Diagnosing Sjögren's Syndrome

Figure 1:
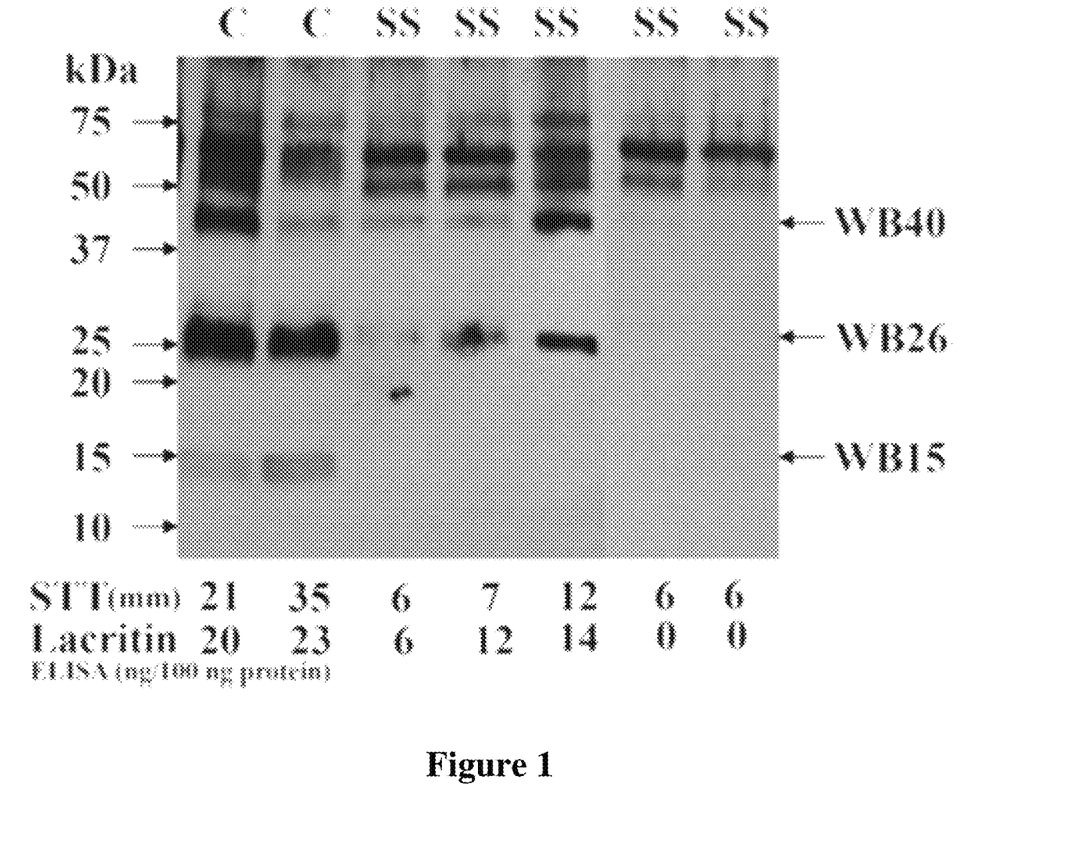
FIG. 1 is a photograph which depicts a Western blot analysis of human tear samples for lacritin according to one aspect of the present inventive subject matter.

Applicants have found that reduced levels of monomeric lacritin and increased levels of cross-linked lacritin dimers and other polymers in tears from Sjögren's Syndrome ("SS") patients compared to age-matched controls are highly correlated with clinical signs of dry eye. In addition, Applicants have shown that measurement of tear lacritin levels are equivalent or better than standard clinical measures for diagnosing Sjögren's Syndrome-associated dry eye. FIG. 1 shows representative Western blot and Schirmer Tear Test data obtained from SS patients and age-matched controls, showing the inactive, tissue transglutaminase-generated complexes of lacritin >40 kDa labeled "WB40", a proteolytically cleaved fragment of ~15 kDa labeled "WB15", and the active lacritin monomer of ~26 kDa labeled "WB26". As the Western blot analysis demonstrates, bands for monomeric lacritin are either missing or reduced in intensity in SS patients compared to age-matched controls. The Schirmer Tear Test values correlated with reduced tear production in SS patients, while quantitation of tear lacritin in the lacritin ELISA corresponds with reduced monomeric lacritin visualized by Western blot analysis.

In addition to the lacritin work discussed above, Applicants used a synthetic peptide to produce lacritin-c specific polyclonal antibodies in rabbits and determined that their anti-lacritin-c antibodies detect putative lacritin-c proteins in human tears. Additionally, Applicants have determined that the protein banding patterns in tears from Sjögren's Syndrome patients are different compared to normal tears when exposed to anti-lacritin-c antibodies, providing novel methods and reagents for detecting lacritin-c as a biomarker for Sjögren's Syndrome.

Thus, the inventive subject matter relates to a method for diagnosing Sjögren's Syndrome in a subject, comprising: (a) detecting whether lacritin-c is present in a tear sample obtained from a human subject by contacting the tear sample with a non-human animal anti-lacritin-c antibody and detecting binding between lacritin-c and said antibody; and (b) diagnosing the subject with Sjögren's Syndrome when lacritin-c in the tear sample is not detected.

The inventive subject matter relates to an additional method for diagnosing Sjögren's Syndrome in a subject, comprising: (a) obtaining a tear sample from a human subject; (b) detecting whether lacritin is present in the tear sample by contacting the tear sample with antibody to SEQ ID NO. 1, and detecting binding between lacritin and said antibody to SEQ ID NO. 1; (c) detecting whether lacritin-c is present in the tear sample by contacting the tear sample with antibody to SEQ ID NO. 2 and detecting binding between lacritin-c and said antibody to SEQ ID NO. 2; and (d) diagnosing the subject with Sjögren's Syndrome when lacritin or lacritin-c in the tear sample is not detected.

The inventive subject matter relates to a further method for diagnosing Sjögren's Syndrome in a subject, comprising: (a) in a tear sample of a subject suspected to suffer from Sjögren's Syndrome, determining the amount of lacritin-c present in said tear sample with an immunoassay, wherein said immunoassay comprises: (i) contacting the sample with an anti-lacritin-c antibody; (ii) measuring the amount of bound lacritin-c in the sample; and (b) comparing the amount of lacritin-c with reference amount(s) obtained from one or more sample(s) of subject(s) known not to suffer from Sjögren's Syndrome, wherein Sjögren's Syndrome is diagnosed if the amount of lacritin-c is decreased as compared to said reference amount(s).

Finally, the inventive subject matter relates to an additional method for diagnosing Sjögren's Syndrome in a subject, comprising: (a) in a tear sample of a subject suspected to suffer from Sjögren's Syndrome, determining the amount of lacritin and the amount of lacritin-c present in said tear sample with an immunoassay, wherein said immunoassay comprises: (i) contacting the sample with antibody microarray comprising an anti-lacritin antibody and an anti-lacritin-c antibody; (ii) measuring the amounts of bound lacritin and lacritin-c in the sample; and (b) comparing the amounts of lacritin and lacritin-c with reference amounts obtained from samples from subject(s) known not to suffer from Sjögren's Syndrome, wherein Sjögren's Syndrome is diagnosed if the amounts of both lacritin and lacritin-c are decreased as compared to said reference amounts.

D. Inventive Compounds for Detecting Latritin-c

Applicants have developed novel compounds, antibodies termed the "I3 antibody" herein, which selectively bind to SEQ ID NO 2, a synthetic peptide derived from Intron 3 of Lacritin-c. Such compounds can further be labeled, radiographically, using chemiluminescence, or with binding sites of flourescent secondary antibodies, in order to make detection of Lacritin-c binding possible. Such novel compounds are an additional embodiment of the present inventive subject matter.

EXAMPLES

The following examples are illustrative of the inventive subject matter and are not intended to be limitations thereon.

Example 1

Production of Antibodies.

The synthetic peptide EDASSDSTGADPAQEAGTS was used to make anti-lacritin polyclonal antibodies in New Zealand white rabbits, also called the "N-Term Antibody" herein. The synthetic peptide SKSLSLCQINN-LEKSLAAGPHHTSTHRDKPG was used to make anti-lacritin-c polyclonal antibodies in New Zealand white rabbits, also called the "I3 Antibody" herein. A synthetic peptide of 19 amino acids in the N-94/C-6 C-terminus of lacritin was used to make anti-lacritin polyclonal antibodies in goats, also called the "Lacripep Antibody" herein. All antibodies were produced using standard techniques well known in the art.

Example 2

Western Blot Analysis of Human Tear Samples for Lacritin.

Human tear samples from 10 patients with Sjögren's Syndrome (SS) and 10 age-matched controls (C) were analyzed by Western blot, Schirmer Tear Test, and ELISA.

ELISA was used to assess total tear lacritin. For assay of tear samples, 100 ng total tear protein was coated in each well. To generate a standard curve of recombinant lacritin, each plate contained triplicate wells to which 2, 4, 6, 8, 10, 12, 14, or 16 ng protein was added. Wells were washed, blocked with PBS-Tween (PBS with 0.3% Tween-20 [PBS-T]), and then incubated for 1 hour at 37° C. with 100 μL anti-Pep Lac N-Term antiserum diluted 1:3,000 in PBS-T. After washing three times with PBS-T, horseradish peroxidase (HRP)-conjugated goat anti-rabbit IgG (MP Biomedicals, Solon, Ohio) diluted 1:1,000 in PBS-T was added for 1 hour (37° C.). Plates were washed three times with PBS-T, and then bound antibody was measured after incubation for 10 minutes with 100 μL OPD substrate (Acros Organics, Geel, Belgium) by absorbance at 415 nm (model 680; Bio-Rad, Hercules, Calif.).

Western blot was used to detect active lacritin monomer (~25 kDa), active lacritin fragment (~12-15 kDa), and inactive, tissue transglutaminase-generated lacritin (>40 kDa). Tear samples were loaded on Any kD™ Mini-PROTEAN® TGX™ Precast Protein Gels (Bio-Rad), electrophoresed at 200 V, and transferred to nitrocellulose (Protran BA 83; Whatman, Dassel, Germany). Blots were blocked with PBS-T, incubated with anti-Lac Pep N-Term (1:1,000 dilution in PBS-T) for 1 hour at room temperature, rinsed with PBS-T, and incubated for 1 hour at room temperature with HRP-138 conjugated goat anti-rabbit IgG (MP Biomedicals) diluted 1:5,000 in PBS-T.

Western blots shown the drawings herein in black and white were rinsed with PBS-T and developed via chemiluminescence with Pierce ECL Western Blotting Substrate (Thermo Fisher Scientific Inc., Rockford, Ill.). Western blots shown in the drawings herein in color were developed with fluorescent secondary antibodies and imaged by a LI-COR Odyssey CLx Imaging System.

The signal intensity of lacritin bands was determined by multiplying the area of the band with the average pixel intensity, which provided volume-sum intensity for each band. The signal intensity of the 12-15 kDa, 25 kDa and >40 kDa bands from each individual's tear sample was quantified using Image J. The signal intensity value of each band was expressed as area pixel density. Finally, in vivo confocal microscopy was used to assess nerve fiber density and nerve fiber length.

As shown in FIG. 1, the "WB26" bands are the active lacritin monomer and the "WB40" bands are inactive >40 kDa dimer and larger complexes of lacritin. The "WB15" bands are a proteolytically cleaved fragment of lacritin. Tears eluted from Schirmer strips were obtained from 10 SS patients and 10 age-matched controls. Applicants found that active tear lacritin was significantly reduced in SS patients ($4.31 \pm 5.73$ ng/100 ng [SS] vs. $18.17 \pm 4.57$ ng/100 ng total tear protein [controls]; P<0.001), while inactive lacritin was increased. Nerve fiber density ($21.00 \pm 10.85$ vs. $33.60 \pm 9.29$; P=0.02) and nerve fiber length ($4.31 \pm 2.09$ vs. $7.46 \pm 2.62$; P<0.001) were significantly decreased in SS patients compared to controls. Both reduced nerve fiber length (r=0.71, p<0.001) and nerve fiber density (r=0.68, p<0.001) were highly correlated with reduced tear lacritin. Similarly, total tear lacritin was highly correlated with tear secretion (r=0.72, p<0.001), ocular staining (r=−0.78, p<0.001), corneal sensitivity (r=0.69, p<0.001) and tear breakup time (r=0.49, p=0.03).

As shown in Table 1, Applicants found that overall levels of tear lacritin were profoundly reduced in the tears of SS patients. Similarly, both the active cleaved fragment and lacritin monomer were significantly decreased, while inactive lacritin was increased in SS tears. Shown graphically, levels of the cleaved fragment, migrating at approximately 15 kDa on Western Blots (WB15), were 14% lower in SS versus control tears (95% CI: 6~22%), while lacritin monomer, migrating at approximately 26 kDa on Western Blots (WB26), was 26% lower than control eyes (95% CI: 16~36%). Perhaps most compelling, inactive lacritin cross-linked by tissue transglutaminase in tears and migrating as multiple bands around 40 kDa on Western Blots (WB40), was 39% higher in SS patients compared to controls (95% CI: 31~84%).

TABLE 1

Comparison of total lacritin and percent expression of lacritin species

| Lacritin | Control Mean (SD) | SS Mean (SD) | p value |
|---|---|---|---|
| ELISA* | 18.17 (4.57) | 4.31 (5.73) | <0.001 |
| WB15[†] | 15.0 (7.0) | 2.0 (6.0) | <0.01 |
| WB26[†] | 34.0 (11.0) | 16.0 (10.0) | <0.01 |
| WB40[†] | 51.0 (12.0) | 82.0 (10.0) | <0.001 |

*Total tear lacritin measured by ELISA and expressed as ng/100 ng total protein
[†]Percent expression of 15 kDa, 26 kDa and >40 kDa lacritin species assessed by Western blot (WB) and quantified by densitometry Example 3

Additional Western Blot Analysis of Human Tear Samples for Lacritin.

Figure 2:
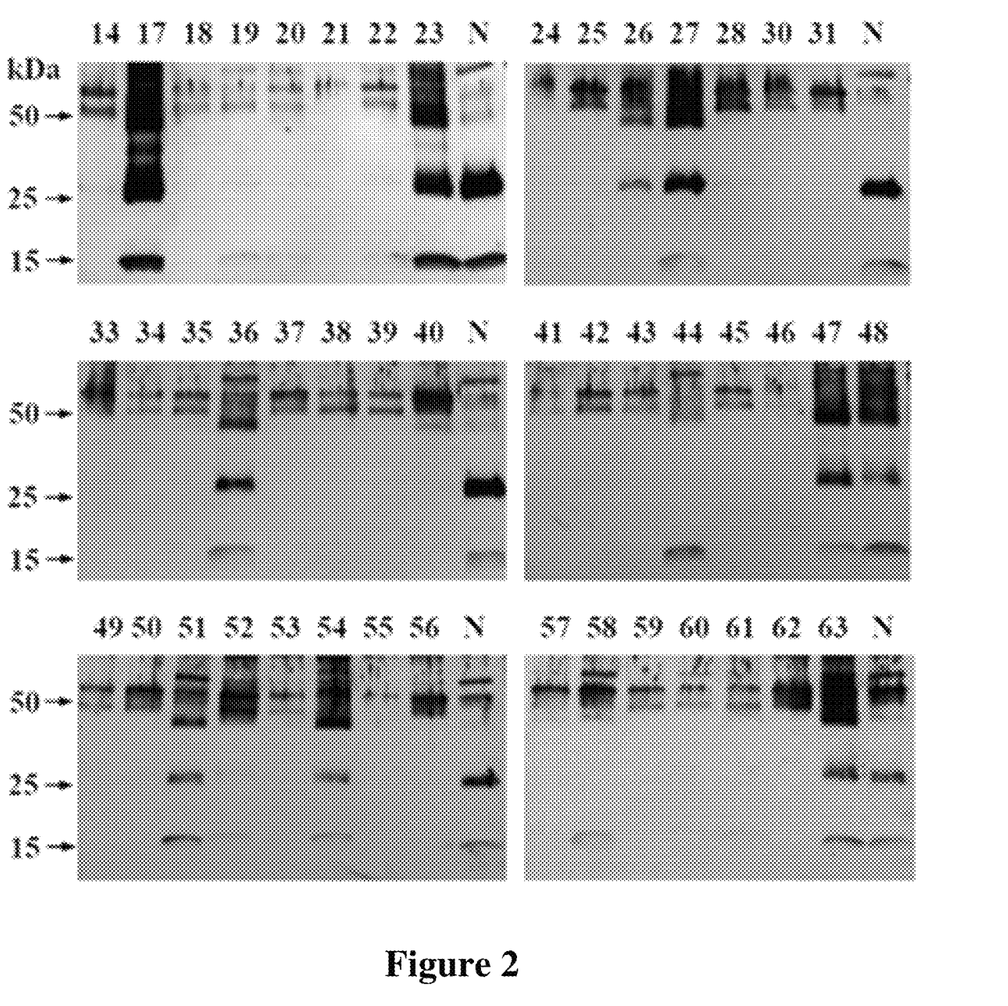
FIG. 2 is a series of photographs which depict Western blot analysis of human tear samples for lacritin according to one aspect of the present inventive subject matter.

A collection of 46 Schirmer Tear Test strips from the Sjögren's International Collaborative Clinical Alliance (SICCA) in vials labeled UCSF ASB were analyzed. Tear samples were eluted, total protein determined by the BCA assay, and tear protein samples normalized to 200 µg/mL. 4 µg of each sample was loaded on SDS PAGE, transferred to nitrocellulose, challenged with anti-lacritin antibodies, and developed by chemiluminescence. FIG. 2 is a summary panel of the Western blots challenged with anti-lacritin antibodies for 46 samples from the SICCA collection along with 5 normal tear samples, where N denotes normal tear samples.

As shown in FIG. 2, higher molecular weight complexes of inactive lacritin can be seen in all 46 SS samples while monomeric lacritin is not detected in 36 (78%) of the SS samples. Reduced levels of monomeric lacritin can be seen in 4 (9%) of the SS samples and 6 (13%) of the SS samples showed normal monomeric levels. In a preliminary analysis of tear lacritin from 46 patients diagnosed with Sjögren's Syndrome, 87% exhibited reduced levels of active lacritin while 13% showed normal levels of monomeric lacritin.

Example 4

Comparison to Prior Art Diagnostic Tests.

Compared to current clinical readouts used to assess the signs and symptoms of SS dry eye, lacritin and its isoforms performed as well or better than traditional diagnostic tests to differentiate SS dry eye from controls. As shown in Table 2, using optimized cutoff values for total lacritin, lacritin monomer and inactive lacritin species, SS cases were correctly identified with a sensitivity of 100.00% and specificities of 87.50% (95% CI: 60.00~100.00%), 70.00% (95% CI: 40.00~100.00%), and 87.5% (95% CI: 60.00~100.00%), respectively. The OSS, currently the primary objective clinical test used to diagnose the ocular component of SS, had a sensitivity of 90.00% (73.86~100.00%) and corresponding specificity of 89.47% (72.23~100.00%) when using the cutoff of >3, as specified by the current American College of Rheumatology diagnostic criteria. As such, the sum of sensitivity and specificity for OSS was 8.03% lower than that of total tear lacritin and its inactive isoform (WB40), which had sums equal to 187.50%. It was also noted that the AUCs of lacritin ELISA (AUC=0.98) and inactive lacritin WB40 (AUC=0.97) were slightly higher than any of the clinical parameters used to differentiate SS patients from the healthy controls.

TABLE 2

Diagnostic performance of tear lacritin and clinical test using standard and optimized cutoffs

| Tested variables | | AUC (95% CI) | Cutoff (95% CI) | Sensitivity (%) (95% CI) | Specificity (%) (95% CI) | Sensitivity + Specificity |
|---|---|---|---|---|---|---|
| Diagnostic Performance of Tear Lacritin | | | | | | |
| Lacritin | ELISA | 0.98 (0.94~1.00) | 14.50 (5.05~16.50) | 100.00 (—)* | 87.50 (60.00~100.00) | 187.50 |
| | WB15 | 0.90 (0.75~1.00) | 3% (2%~20%) | 83.33 (58.85~100.00) | 100.00 (—) | 183.33 |
| | WB26 | 0.95 (0.84~1.00) | 30% (11%~41%) | 100.00 (—) | 75.00 (40.00~100.00) | 175.00 |
| | WB50 | 0.97 (0.90~1.00) | 62% (60%~74%) | 100.00 (—) | 87.50 (60.00~100.00) | 187.50 |
| Diagnostic Performance of Traditional Clinical Tests | | | | | | |
| OSDI | Standard | 0.86 (0.74~0.98) | 20 | 66.67 (42.86~87.50) | 78.95 (57.91~95.24) | 145.62 |
| | Optimized | | 18.05 (12.03~53.10) | 77.78 (57.14~94.74) | 78.95 (57.91~95.24) | 156.73 |
| Schir | Standard | 0.95 (0.88~1.00) | 5 | 50.00 (26.32~71.41) | 100.00 (—) | 150.00 |
| | Optimized | | 8.50 (6.50~15.00) | 85.00 (66.70~100.00) | 94.74 (83.33~100.0) | 179.74 |
| OSS | Standard | 0.96 (0.74~0.98) | 3 | 90.00 (73.68~100.00) | 89.47 (72.23~100.0) | 179.47 |
| | Optimized | | 4.50 | 80.00 (59.28~95.24) | 100 (—) | 180.00 |
| TBUT | Standard | 0.75 (0.59~0.92) | 10 | 100.00 (—) | 0.00 (—) | |
| | Optimized | | 2.5 (2.50~3.00) | 65.00 (45.00~85.00) | 94.74 (84.21~100) | 159.74 |
| CST | Optimized | 0.88 (0.77~0.99) | 4.25 (3.75~5.25) | 80.00 (55.00~100.00) | 88.89 (55.56~100) | 168.89 |

Example 5

Lacritin Splice Variants and Antibodies Thereto.

Figure 3:
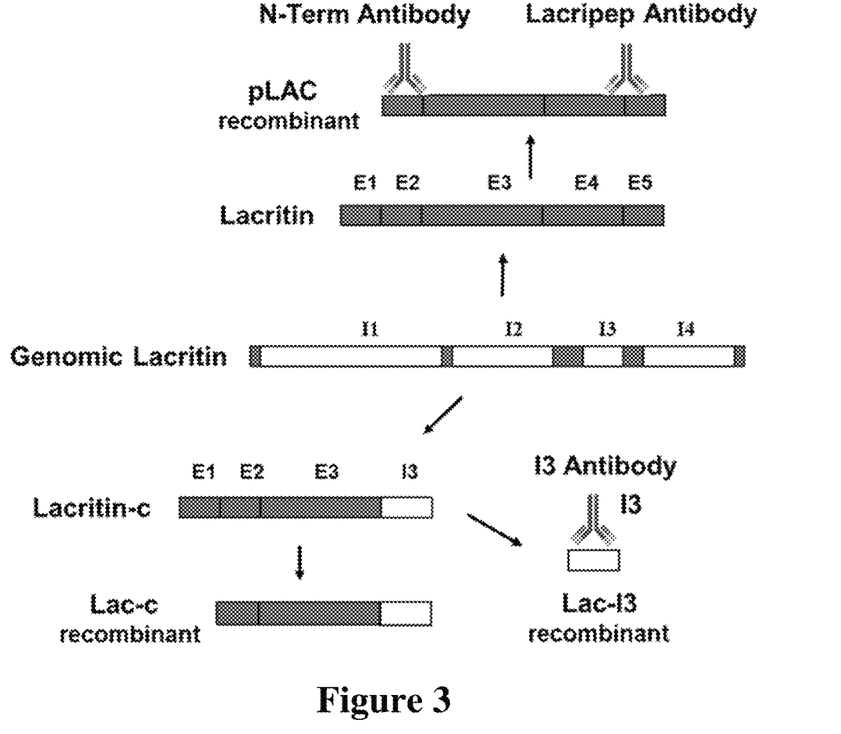
FIG. 3 is a drawing which depicts natural and recombinant lacritin splice variants, and pictorially depicts the binding regions for the Lacripep, N-Term, and I3 antibodies according to one aspect of the present inventive subject matter.

FIG. 3 illustrates the genomic DNA of lacritin and the splice variant lacritin-c. Genomic lacritin contains four Intron DNA sequences (I) separating five Exon DNA sequences (E) coding for amino acids. Following transcription, the five Exons within the mRNA are spliced together to produce a continuous coding sequence for lacritin protein. Upon secretion by acinar cells in the lacrimal gland, the signal peptide sequences in Exon 1 are cleaved off to produce mature lacritin found in human tears.

A splice variant of lacritin containing the first three exons of lacritin and DNA sequences coding for 39 amino acids in Intron 3 is known as lacritin-c. Lacritin-c is composed of coding sequences for the first three lacritin exons, which is then spliced into an open reading frame coding for 39 new amino acids derived from intron 3 (I3), followed by a stop codon.

The unique amino acid sequences in lacritin-c are not found in lacritin or other known splice variants, which provided Applicants with an opportunity to create unique antibodies that detect only lacritin-c in tear samples using Western blot analysis. A synthetic peptide, SEQ ID NO. 2, present in lacritin-c but not other lacritin species, was used to make lacritin-c specific polyclonal antibodies in New Zealand white rabbits.

Example 6

Western Blot Analysis of Tear Samples for Splice Variant Lacritin-c.

Figure 4:
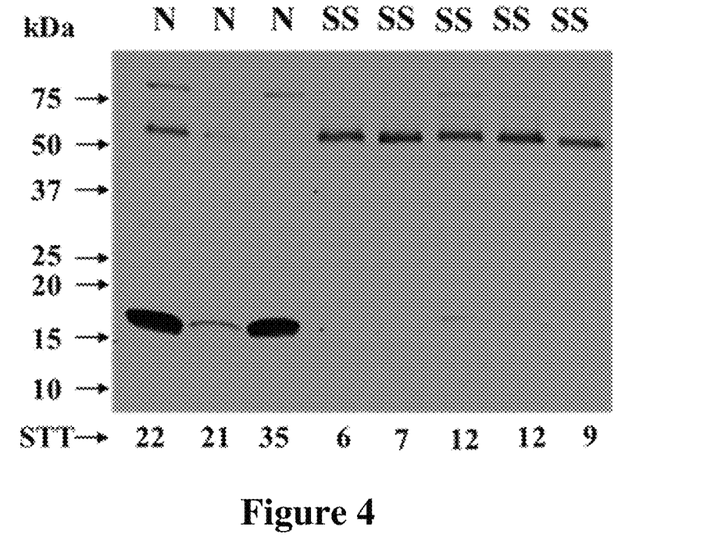
FIG. 4 is a photograph which depicts a Western blot analysis of human tear samples for lacritin-c according to one aspect of the present inventive subject matter.

Human tear samples from patients with Sjögren's Syndrome (SS) and age-matched controls (N) were eluted, loaded on SDS PAGE, transferred to nitrocellulose, challenged with anti lacritin-c antibodies, and developed by chemiluminescence. The Western blot shown in FIG. 4 shows the results for tear samples challenged with anti-lacritin-c antibodies, which reveals a dramatic difference in banding patterns in tear samples from Sjögren's Syndrome patients compared to normal tears. Tears from SS patients show a major band migrating at approximately 50 kDa while normal tears show a predominant band migrating at approximately 15 kDa, the expected molecular weight of monomeric lacritin-c. The monomeric lacritin-c is missing in all tested SS patients, and the Schirmer Tear Test values for the same SS patients correlate with reduced tear production, providing a second biomarker for the diagnosis of Sjögren's Syndrome-associated Dry Eye Disease.

Example 7

Western Blot Analysis of Human Tears with Lacritin Antibodies.

Figure 5:
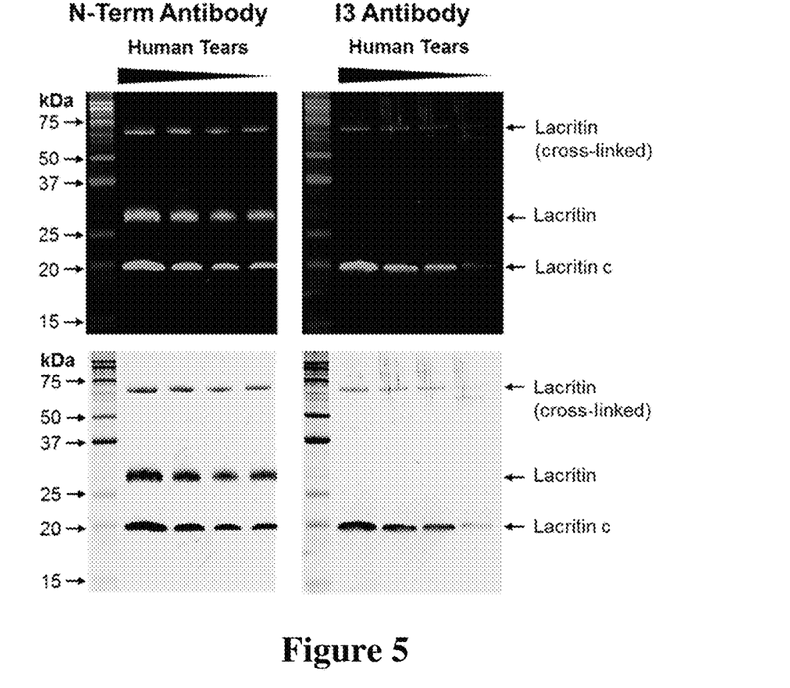
FIG. 5 is a series of photographs which depict Western blot analysis of human tears with lacritin antibodies according to one aspect of the present inventive subject matter.

Tears collected from healthy individuals using Schirmer strips were eluted by centrifugation and total protein concentrations determined by the BCA assay as described above. Tear proteins normalized to 200 μg/ml were separated by SDS PAGE, transferred to nitrocellulose and challenged by N-Term lacritin antibodies and 13 lacritin-c antibodies. Western blots shown in FIG. 5 were prepared as described above, developed by fluorescent secondary antibodies, and imaged by a LI-COR Odyssey CLx Imaging System. The N-Term lacritin antibodies detected lacritin monomers, cross-linked lacritin multimers, and lacritin-c. On the other hand, 13 lacritin-c antibodies detected lacritin-c and not lacritin monomers.

Example 8

Western Blot Quantitative Analysis.

Figure 6:
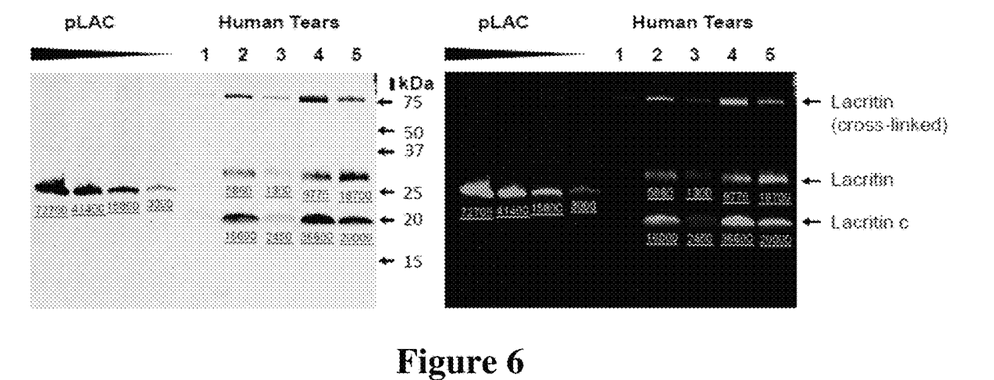
FIG. 6 is a pair of photographs which depict Western blot quantitative analysis of human tear samples as compared to purified recombinant lacritin of known concentrations according to one aspect of the present inventive subject matter.

Tears collected from healthy individuals using Schirmer strips were eluted by centrifugation and total protein concentrations determined by the BCA assay. Tear proteins normalized to 200 µg/ml and purified recombinant lacritin of known concentrations were separated by SDS PAGE, transferred to nitrocellulose and challenged by N-Term lacritin antibodies. Western blots shown in FIG. 6 were prepared as described above, developed by fluorescent secondary antibodies, and imaged by a LI-COR Odyssey CLx Imaging System.

Figure 7:
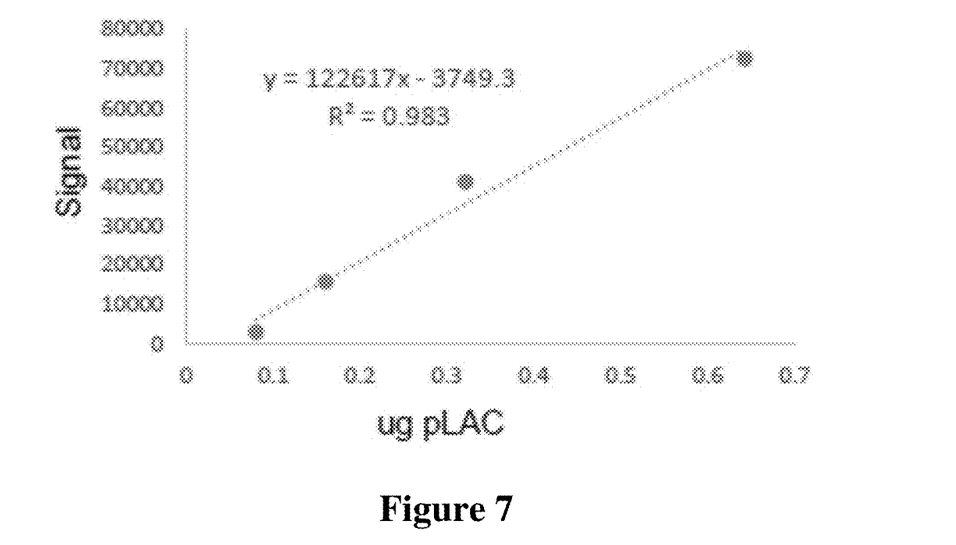
FIG. 7 is a graph depicting a standard curve for determining concentrations of tear lacritin proteins according to one aspect of the present inventive subject matter.

Specific protein bands for lacritin, lacritin-c, and cross-linked polymers of lacritin were quantified by pixel density with the Odyssey CLx Imaging System. Decreasing concentrations of purified recombinant lacritin were run on each blot and quantified to generate the standard curve shown in FIG. 7, which was then used to determine concentrations of tear lacritin proteins. Table 3 shows the quantitation of several samples using the standard curve generated as described above.

TABLE 3

Exemplary quantitation of tear lacritin proteins.

| Tear Sample | Lacritin µg | Lacritin % Protein | Lacritin-c µg | Lacritin-c % Protein |
|---|---|---|---|---|
| 1 | N/D | N/D | N/D | N/D |
| 2 | 0.078 | 4.7 | 0.161 | 9.64 |
| 3 | 0.041 | 2.5 | 0.050 | 3.0 |
| 4 | 0.110 | 6.6 | 0.329 | 19.7 |
| 5 | 0.183 | 11.0 | 0.194 | 11.8 |

N/D = Not Detected; negative control

Example 9

A Diagnostic Test for Sjögren's Syndrome.

Applicants expect that the predominant band migrating at approximately 15 kDa found in Example 6, which has the expected molecular weight of monomeric lacritin-c, is in fact lacritin-c. A diagnostic reagent comprising an anti-lacritin-c antibody raised in rabbit, goat, or other animal is found to accurately and specifically detect lacritin-c in tear samples. Lacritin-c is found to be an effective biomarker for diagnosing Sjögren's Syndrome, as well as determining the prognosis and severity of Sjögren's Syndrome disease when quantified.

Example 10

A Kit for Diagnosing Sjögren's Syndrome.

Tear proteins are collected on modified Schirmer strips and incubated with a predetermined titer of antibodies embedded on the strips, and developed with a colorimetric reagent to provide a qualitative positive/negative test for threshold concentrations of active tear lacritin and/or lacritin-c. A non-obvious and unique attribute of this diagnostic test is that lacritin antibodies embedded on the strips under non-denaturing conditions do not detect the inactive >40 kDa cross-linked polymers of lacritin. Further, the same Schirmer strip used for the Schirmer Tear Test is used for the lacritin dipstick immunoassay, minimizing patient intrusions and cost.

Example 11

Multiplex Western Blot Analysis.

Figure 8:
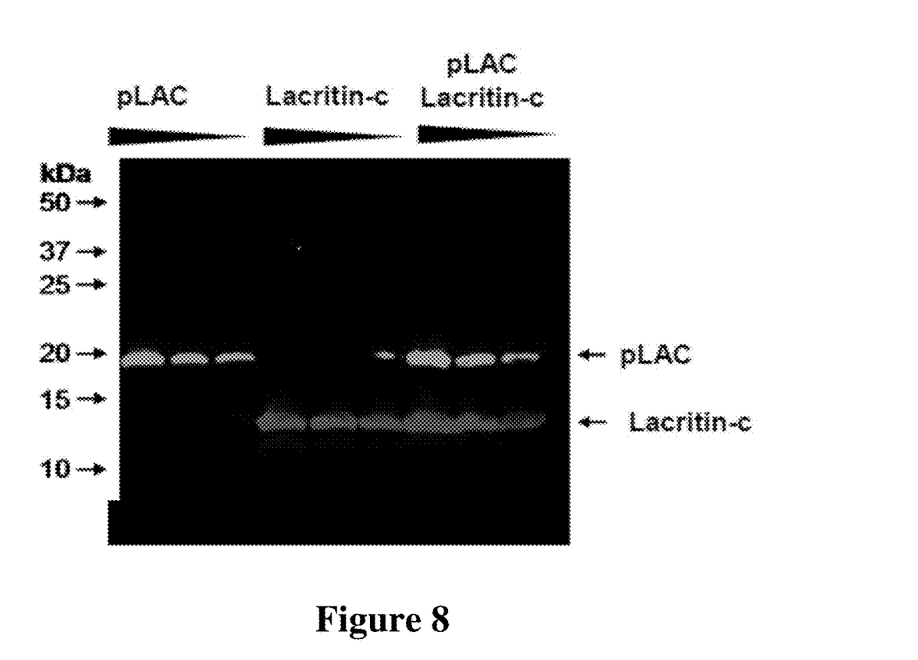
FIG. 8 is a photograph which depicts a multiplex Western blot analysis according to one aspect of the present inventive subject matter.

In order to analyze both lacritin and lacritin-c more efficiently and cost-effectively on the same blot, Lacripep anti-lacritin antibodies were produced in goat and used with rabbit 13 anti-lacritin-c antibodies to enable detection with secondary antibodies labeled with spectrally-distinct NIR fluorescent dyes. It was expected that the fluorescent bands would be quantified and differential expression of the two proteins in tears from Sjögren's Syndrome patients would be quantified and compared to control tears. Applicants prepared recombinant lacritin in decreasing concentrations, which were run in the first three lanes and decreasing concentrations of lacritin-c in the middle three lanes. Both proteins were mixed at the same decreasing concentrations and were run together in the last three lanes. The protein samples were separated by SDS PAGE, transferred to nitrocellulose and challenged by a mixture of Lacripep lacritin and 13 lacritin-c antibodies at the same time on the same blot. A Western blot as shown in FIG. 8 was prepared as described above, developed by fluorescent secondary antibodies unique to lacritin and lacritin-c, and imaged by a LI-COR Odyssey CLx Imaging System. In FIG. 8, the red bands depict 13 lacritin-c antibody binding, while the green bands depict Lacripep lacritin antibody binding, demonstrating specificity of the respective antibodies: Lacripep antibodies detected only lacritin and 13 antibodies detected only lacritin-c.

REFERENCES

The following literature references are believed to useful to an understanding of the inventive subject matter in the context of its place in the relevant art. Citation here is not to be construed as an assertion or admission that any reference cited is material to patentability of the inventive subject matter. Applicants will properly disclose information material to patentability in an Information Disclosure Statement. Each of the following documents is hereby incorporated by reference in its entirety in this application.

1. del Castillo J M B, Wasfy M A, Fernandez C, Garcia-Sanchez J. An in vivo confocal masked study on corneal epithelium and subbasal nerves in patients with dry eye. Invest Ophthalmol Vis Sci 2004; 45:3030-3035.
2. Labbë A, Liang Q, Wang Z, et al. Corneal nerve structure and function in patients with non-Sjögren dry eye: clinical correlations. Invest Ophthalmol Vis Sci 2013; 54:5144-5150.
3. Eskandari F, Webster J I, Sternberg E M. Neural immune pathways and their connection to inflammatory diseases. Arthritis Res Ther 2003; 5:251-65.
4. Olofsson P S, Rosas-Ballina M, Levine Y A, Tracey K J. Rethinking inflammation: neural circuits in the regulation of immunity. Immunol Rev 2012; 248:188-204.
5. Knox S M, Lombaert I M, Haddox C L, et al. Parasympathetic stimulation improves epithelial organ regeneration. Nat Commun 2013; 4:1494.
6. Sanghi S, Kumar R, Lumsden A, et al. cDNA and genomic cloning of lacritin, a novel secretion enhancing factor from the human lacrimal gland. J Mol Biol 2001; 310: 127-39.
7. Velez V F, Romano J A, McKown R L, et al. Tissue transglutaminase is a negative regulator of monomeric lacritin bioactivity. Invest Ophthalmol Vis Sci 2013; 54:2123-32.

8. McKown R L, Wang N, Raab R W, et al. Lacritin and other new proteins of the lacrimal functional unit. Exp Eye Res 2009; 88:848-58.
9. Fujii A, Morimoto-Tochigi A, Walkup R D, Shearer T R, Azuma M. Lacritin-induced secretion of tear proteins from cultured monkey lacrimal acinar cells. Invest Ophthalmol Vis Sci 2013; 54:2533-40.
10. McKown R L, Coleman Frazier E V, Zadrozny K K, et al. A cleavage-potentiated fragment of tear lacritin is bactericidal. J Biol Chem 2014; 289:22172-82.
11. Samudre S, Lattanzio F A, Jr., Lossen V, et al. L 361 Lacritin, a novel human tear glycoprotein, promotes sustained basal tearing and is well tolerated. Invest Ophthalmol Vis Sci 2011; 52:6265-70.
12. Wang N, Zimmerman K, Raab R W, et al. Lacritin rescues stressed epithelia via rapid forkhead box O3 (FOXO3)-associated autophagy that restores metabolism. J Biol Chem 2013; 288:18146-61.
13. Aluru S V, Agarwal S, Srinivasan B, et al. Lacrimal proline rich 4 (LPRR4) protein in the tear fluid is a potential biomarker of dry eye Syndrome. PLoS One 2012; 7:e51979.
14. Nichols J J, Green-Church K B. Mass spectrometry-based proteomic analyses in contact lens related dry eye. Cornea 2009; 28:1109-17.
15. Vijmasi T, Chen F Y, Balasubbu S, et al. Topical administration of lacritin is a novel therapy for aqueous-deficient dry eye disease. Invest Ophthalmol Vis Sci 2014; 55:5401-9.
16. Shiboski S, Shiboski C, Criswell L, et al. American College of Rheumatology classification criteria for Sjögren's Syndrome: A data-driven, expert consensus approach in the Sjögren's International Collaborative Clinical Alliance Cohort. Arthritis Care Res 2012; 64:475-487.
17. Whitcher J P, Shiboski C H, Shiboski S C, et al. A simplified quantitative method for assessing keratoconjunctivitis sicca from the Sjögren's Syndrome International Registry. Am J Ophthalmol 2010; 149:405-415.
18. Degasperi A, Birtwistle M R, Volinsky N, Rauch J, Kolch W, Kholodenko B N. Evaluating strategies to normalise biological replicates of Western blot data. PLoS One 2014; 9:e87293.
19. Robin X, Turck N, Hainard A, et al. Package "pROC". Version 1.8. 2015.
20. Canty A, Ripley B. Package "boot". Version 1.3-17. 2015.
21. Dartt D A. Neural regulation of lacrimal gland secretory processes: relevance in dry eye diseases. Prog Retin Eye Res 2009; 28:155-77.
22. Rhiner C, Gysi S, Frohli E, Hengartner M O, Hajnal A. Syndecan regulates cell migration and axon guidance in C. elegans. Development 2005; 132:4621-33.
23. Tavakoli M, Quattrini C, Abbott C, et al. Corneal confocal microscopy a novel noninvasive test to diagnose and stratify the severity of human diabetic neuropathy. Diabetes Care 2010; 33:1792-1797.
24. Erie J C, McLaren J W, Hodge D O, Bourne W M. Recovery of corneal subbasal nerve density after PRK and LASIK. Am J Ophthalmol 2005; 140:1059-1064.
25. Oliveira-Soto L, Efron N. Morphology of corneal nerves in soft contact lens wear. A comparative study using confocal microscopy. Ophthalmic Physiol Opt 2003; 23:163-74.
26. Patel D V, Tavakoli M, Craig J P, Efron N, McGhee C N. Corneal sensitivity and slit scanning in vivo confocal microscopy of the subbasal nerve plexus of the normal central and peripheral human cornea. Cornea 2009; 28:735-740.
27. Patel S V, McLaren J W, Hodge D O, Bourne W M. Confocal microscopy in vivo in corneas of long-term contact lens wearers. Invest Ophthalmol Vis Sci 2002; 43:995-1003.
28. Cruzat A, Pavan-Langston D, Hamrah P. In vivo confocal microscopy of corneal nerves: analysis and clinical correlation. Semin Ophthalmol 2010; 25:171-7.
29. Villani E, Galimberti D, Viola F, Mapelli C, Ratiglia R. The cornea in Sjögren's Syndrome: an in vivo confocal study. Invest Ophthalmol Vis Sci 2007; 48:2017-22.
30. Tuisku I S, Konttinen Y T, Konttinen L M, Tervo T M. Alterations in corneal sensitivity and nerve morphology in patients with primary Sjögren's Syndrome. Exp Eye Res 2008; 86:879-885.
31. Tuominen I S, Konttinen Y T, Vesaluoma M H, Moilanen J A, Helinto M, Tervo T M. Corneal innervation and morphology in primary Sjögren's Syndrome. Invest Ophthalmol Vis Sci 2003; 44:2545-9.
32. Zhang M, Chen J, Luo L, Xiao Q, Sun M, Liu Z. Altered corneal nerves in aqueous tear deficiency viewed by in vivo confocal microscopy. Cornea 2005; 24:818-24.
33. Koo B S, Lee D Y, Ha H S, Kim J C, Kim C W. Comparative analysis of the tear protein expression in blepharitis patients using two-dimensional electrophoresis. J Proteome Res. 2005 May-June; 4(3):719-24.
34. McNamara N A, Ge S, Lee S M, Enghauser A M, Kuehl L, Chen F Y, Gallup M, McKown R L. Reduced Levels of Tear Lacritin Are Associated With Corneal Neuropathy in Patients With the Ocular Component of Sjögren's Syndrome. Invest Ophthalmol Vis Sci. 2016 Oct. 1; 57(13): 5237-5243.
35. Ma, P., S. L. Beck, R. W. Raab, R. L. McKown, G. L. Coffman, A. Utani, W. J. Chirico, A. C. Rapraeger, and G. W. Laurie. (2006) Heparanase deglycanation of syndecan-1 is required for binding of epithelial-restricted prosecretory mitogen "lacritin". J. Cell Biol. 174(7): 1097-1106.
36. Wang, J., Wang, N., Xie, J., Walton, S., McKown. R., Raab, R., Ma, P., Beck, S., Coffman, G., Hussaini, and Laurie, G. (2006) Restricted epithelial proliferation by lacritin via PKC-dependent NFAT and mTOR pathways. J. Cell Biol. 174(5): 889-700.
37. Zhang Y, Wang N, Raab R W, McKown R L, Irwin J A, Kwon I, van Kuppevelt T H, Laurie G W. (2013). Targeting of heparanase-modified syndecan-1 by prosecretory mitogen lacritin requires conserved core GAGAL plus heparan and chondroitin sulfate as a novel hybrid binding site that enhances selectivity. J Biol Chem. 288: 12090-101.
38. Karnati R, Laurie D E, Laurie G W. Lacritin and the tear proteome as natural replacement therapy for dry eye. Exp Eye Res. 2013 December; 117:39-52.
39. Wang W, Jashnani A, Aluri S R, Gustafson J A, Hsueh P Y, Yarber F, McKown R L, Laurie G W, Hamm-Alvarez S F, MacKay J A. A thermo-responsive protein treatment for dry eyes. J Control Release. 2015 Feb. 10; 199:156-67.

40. Vijmasi T, Chen F Y, Balasubbu S, Gallup M, McKown R L, Laurie G W, McNamara N A. Topical administration of lacritin is a novel therapy for aqueous-deficient dry eye disease. Invest Ophthalmol Vis Sci. 2014 Jul. 17; 55(8): 5401-9.

41. Laurie, G. W., Olsakovsky, L. A., Conway, B. P., McKown, R. L., Kitagawa, K., and Nichols, J. J. (2008) Dry Eye and Designer Ophthalmic Treatments. Optom Vis Sci. 85(8):643-52.

The inventive subject matter being thus described, it will be obvious that the same may be modified or varied in many ways. Such modifications and variations are not to be regarded as a departure from the spirit and scope of the inventive subject matter, and all such modifications and variations are intended to be included within the scope of the following claims.

What is claimed is:

1. A method for treating Sjögren's Syndrome in a subject suspected to suffer from Sjögren's Syndrome, comprising the steps of:
(1) identifying said subject as being in need of treatment based on:
(a) in a tear sample of said subject, determining or having determined the amount of lacritin-c present in said tear sample with an immunoassay,
wherein said immunoassay comprises: (i) contacting the sample with an anti-lacritin-c antibody; (ii) measuring the amount of bound lacritin-c in the sample;
(b) determining or having determined that the amount of lacritin-c monomer is decreased as compared to the amount of lacritin-c monomer in one or more reference sample amount(s) obtained from subject(s) known not to suffer from Sjögren's Syndrome; and
(2) administering an effective amount of exogenous lacritin-c to treat said subject.

2. The method of claim 1, wherein said anti-lacritin-c antibody is an antibody to SEQ ID NO. 2.

3. A method for treating Sjögren's Syndrome in a subject suspected to suffer from Sjögren's Syndrome, comprising the steps of:
(1) identifying said subject as being in need of treatment based on:
(a) in a tear sample of said subject, determining or having determined the amount of lacritin and the amount of lacritin-c present in said tear sample with an immunoassay,
wherein said immunoassay comprises: (i) contacting the sample with an antibody microarray comprising an anti-lacritin antibody and an anti-lacritin-c antibody; (ii) measuring the amounts of bound lacritin and lacritin-c in the sample;
(b) determining or having determined that the amount of lacritin-c monomer is decreased as compared to the amounts of lacritin monomer and lacritin-c monomer in reference sample amounts obtained from subject(s) known not to suffer from Sjögren's Syndrome; and
(2) administering an effective amount of exogenous lacritin and/or lacritin-c to said subject.

4. The method of claim 3, wherein said anti-lacritin antibody is an antibody to SEQ ID NO. 1, said anti-lacritin-c antibody is an antibody to SEQ ID NO. 2, or both.

* * * * *

SEQUENCE LISTING

```
<160> NUMBER OF SEQ ID NOS: 3

<210> SEQ ID NO 1
<211> LENGTH: 19
<212> TYPE: PRT
<213> ORGANISM: Artificial Sequence
<220> FEATURE:
<223> OTHER INFORMATION: N-terminal sub-sequence of homo sapiens
      lacritin protein
<220> FEATURE:
<221> NAME/KEY: BINDING
<222> LOCATION: (1)..(19)

<400> SEQUENCE: 1

Glu Asp Ala Ser Ser Asp Ser Thr Gly Ala Asp Pro Ala Gln Glu Ala
1               5                   10                  15

Gly Thr Ser

<210> SEQ ID NO 2
<211> LENGTH: 31
<212> TYPE: PRT
<213> ORGANISM: Artificial Sequence
<220> FEATURE:
<223> OTHER INFORMATION: Sub-sequence from the intron 3 domain of homo
      sapiens lacritin-c protein.
<220> FEATURE:
<221> NAME/KEY: BINDING
<222> LOCATION: (1)..(31)

<400> SEQUENCE: 2

Ser Lys Ser Leu Ser Leu Cys Gln Ile Asn Asn Leu Glu Lys Ser Leu
1               5                   10                  15

Ala Ala Gly Pro His His Thr Ser Thr His Arg Asp Lys Pro Gly
            20                  25                  30

<210> SEQ ID NO 3
<211> LENGTH: 138
<212> TYPE: PRT
<213> ORGANISM: Homo sapiens
<220> FEATURE:
<221> NAME/KEY: PEPTIDE
<222> LOCATION: (1)..(138)

<400> SEQUENCE: 3

Met Lys Phe Thr Thr Leu Leu Phe Leu Ala Ala Val Ala Gly Ala Leu
1               5                   10                  15

Val Tyr Ala Glu Asp Ala Ser Ser Asp Ser Thr Gly Ala Asp Pro Ala
            20                  25                  30

Gln Glu Ala Gly Thr Ser Lys Pro Asn Glu Glu Ile Ser Gly Pro Ala
        35                  40                  45

Glu Pro Ala Ser Pro Pro Glu Thr Thr Thr Ala Gln Glu Thr Ser
    50                  55                  60
```

-continued

```
Ala Ala Ala Val Gln Gly Thr Ala Lys Val Thr Ser Ser Arg Gln Glu
 65              70                  75                  80

Leu Asn Pro Leu Lys Ser Ile Val Glu Lys Ser Ile Leu Leu Thr Glu
             85                  90                  95

Gln Ala Leu Ala Lys Ala Gly Lys Gly Met His Gly Gly Val Pro Gly
            100                 105                 110

Gly Lys Gln Phe Ile Glu Asn Gly Ser Glu Phe Ala Gln Lys Leu Leu
        115                 120                 125

Lys Lys Phe Ser Leu Leu Lys Pro Trp Ala
    130                 135
```